(12) United States Patent
Xu

(10) Patent No.: US 9,399,043 B2
(45) Date of Patent: Jul. 26, 2016

(54) COMPOSITION HAVING LIPOLYSIS-PROMOTING EFFECT

(75) Inventor: Shanhua Xu, Eniwa (JP)

(73) Assignee: Final Future International, Inc., Aichi (JP)

( * ) Notice: Subject to any disclaimer, the term of this patent is extended or adjusted under 35 U.S.C. 154(b) by 1104 days.

(21) Appl. No.: 13/261,242

(22) PCT Filed: Sep. 28, 2010

(86) PCT No.: PCT/JP2010/005833
§ 371 (c)(1),
(2), (4) Date: May 24, 2012

(87) PCT Pub. No.: WO2011/039999
PCT Pub. Date: Apr. 7, 2011

(65) Prior Publication Data
US 2012/0244236 A1    Sep. 27, 2012

(30) Foreign Application Priority Data
Oct. 2, 2009  (JP) .................... 2009-230493

(51) Int. Cl.
| A61K 36/064 | (2006.01) |
| A61K 31/721 | (2006.01) |
| A23L 1/30 | (2006.01) |
| A23L 1/305 | (2006.01) |
| A61K 31/7088 | (2006.01) |
| A61K 31/7105 | (2006.01) |
| A61K 35/60 | (2006.01) |
| A61K 36/8998 | (2006.01) |
| A61K 38/39 | (2006.01) |

(52) U.S. Cl.
CPC ............. *A61K 31/721* (2013.01); *A23L 1/3002* (2013.01); *A23L 1/3018* (2013.01); *A23L 1/3053* (2013.01); *A61K 31/7088* (2013.01); *A61K 31/7105* (2013.01); *A61K 35/60* (2013.01); *A61K 36/064* (2013.01); *A61K 36/8998* (2013.01); *A61K 38/39* (2013.01)

(58) Field of Classification Search
None
See application file for complete search history.

(56) References Cited

U.S. PATENT DOCUMENTS

| 2004/0087514 A1* | 5/2004 | Hughes et al. .................. 514/23 |
| 2004/0151738 A1* | 8/2004 | Oriol et al. ................ 424/195.16 |
| 2005/0003026 A1* | 1/2005 | Bok et al. ........................ 424/736 |
| 2009/0197831 A1* | 8/2009 | Rosado Loria et al. ......... 514/55 |

FOREIGN PATENT DOCUMENTS

| CN | 1340302 A | 3/2002 |
| JP | 52-148631 A | 10/1977 |
| JP | 58-109425 A | 6/1983 |
| JP | 59-044323 A | 3/1984 |
| JP | 60-023086 A | 2/1985 |
| JP | 60-023087 A | 2/1985 |
| JP | 61-036226 | 2/1986 |
| JP | 61-036227 A | 2/1986 |
| JP | 02-032127 A | 2/1990 |
| JP | 03-011097 A | 1/1991 |
| JP | 04-144696 A | 5/1992 |
| JP | 08-081382 A | 3/1996 |
| JP | 08-231588 A | 9/1996 |
| JP | 08-245410 A | 9/1996 |
| JP | 08-269088 A | 10/1996 |
| JP | 08-301780 A | 11/1996 |
| JP | 11-228431 A | 8/1999 |
| JP | 2002-000228 A | 1/2002 |
| JP | 2002-275078 A | 9/2002 |
| JP | 2003-095930 A | 4/2003 |
| JP | 2004-307365 A | 11/2004 |
| JP | 2006-045120 A | 2/2006 |
| JP | 2007-106683 A | 4/2007 |
| KR | 10-1998-0070084 A | 10/1998 |
| KR | 10-2007-0113460 A | 11/2007 |
| TW | 200517063 | 6/2005 |
| WO | WO 2005/118619 A1 | 12/2005 |

OTHER PUBLICATIONS

Saiga et al., Angiotensin I—Converting Enzyme-Inhibitory Peptides Obtained from Chicken Collagen Hydrolysate, 2008, J Agric Food Chem, 56: 9586-9591.*
http://www.food.maruha-nichiro.co.jp/english/ffcd/product/pro00500.html.*
Takashi Kadowaki et al., "The role of Adiponectin in Molecular Mechanisms of Diabetes Mellitus/Cardiovascular Disease", Proceedings of the 128th Symposium of the Japanese Association of Medical Sciences "Diabetes Mellitus and Arteriosclerosis", Dec. 2, 2004, p. 34-45.
Noriko Miyano et al., "Kakusan Eiyo Ryoho no Inu.Neko ni Taisuru Rinshi Oyo," Journal of Veterinary Oriental Medicine, 1999, 5:57-60.
Masashi Matsunaga, "Sakana no Kenko Koa to Kinosei Seibun Sake Shirako, Ranso Gaihi no Shokuhin Oyobi Keshohin to Shite no Kinosei," Food Style 21, Jan. 2009, 13(1):55-57.
Ai Saiga-Egus et al., "Antihypertensive Effects and Endothelial Progenitor Cell Activation by Intake of Chicken Collagen Hydrolysate in Pre- and Mild-Hypertension," Biosci. Biotechnol. Biochem., Feb. 2009, 73(2):422-424.

(Continued)

*Primary Examiner* — Terry A. McKelvey
*Assistant Examiner* — Catheryne Chen
(74) *Attorney, Agent, or Firm* — Foley & Lardner LLP

(57) ABSTRACT

An object of the present invention is to provide an orally ingestible composition that has a lipolysis-promoting effect and an angiotensin-converting enzyme (ACE) inhibitory effect and has no problems with safety as a food such as side effects or toxicity, and a food or drink and a supplement comprising the composition. As a result of diligent studies on various food materials to provide a composition for foods having a lipolysis-promoting effect and an ACE inhibitory effect, the present inventor has found that a composition prepared by using a salmon milt extract, a beer yeast extract, a barley grass extract, and chicken collagen in combination has an excellent lipolysis-promoting effect and an ACE inhibitory activity. A food or drink and a supplement having a lipolysis-promoting effect and an ACE inhibitory effect can be provided by using the composition of the present invention as an active ingredient.

4 Claims, 2 Drawing Sheets

(56) References Cited

OTHER PUBLICATIONS

Noriko Miyano et al., "Clinical Application of Nucleic Acid Nutritional Therapy to Dogs and Cats," Journal of Veterinary Oriental Medicine, 1999, 5:57-60, with English translation, 9 pages.

Masashi Matsunaga, "Functionality of Salmon Soft Roe and Ovarian Envelope as Food and Cosmetics," Food Style 21, Jan. 2009, 13(L):55-57, with English translation, 11 pages.

Matsunaga, "Origin of Life-Miracle of Nucleic Acid," Shy Mau Publishing Company, Jul. 10, 1996, with English translation.

Database WPI Week 199745, Thomson Scientific, London, GB; AN 1997-484075 XP002718751, JP H09 224607 A (LS Corp KK) Sep. 2, 1997, abstract.

Li et al., "Application of Collagen," Leather Chemicals, Jun. 25, 2002, 19(3):10-14.

Yang et al., "Research Progress on Medicinal Barley and Its Active Substance," Journal of Triticeae Crops, 2007, 27(6):1154-1158.

* cited by examiner

Figure 1
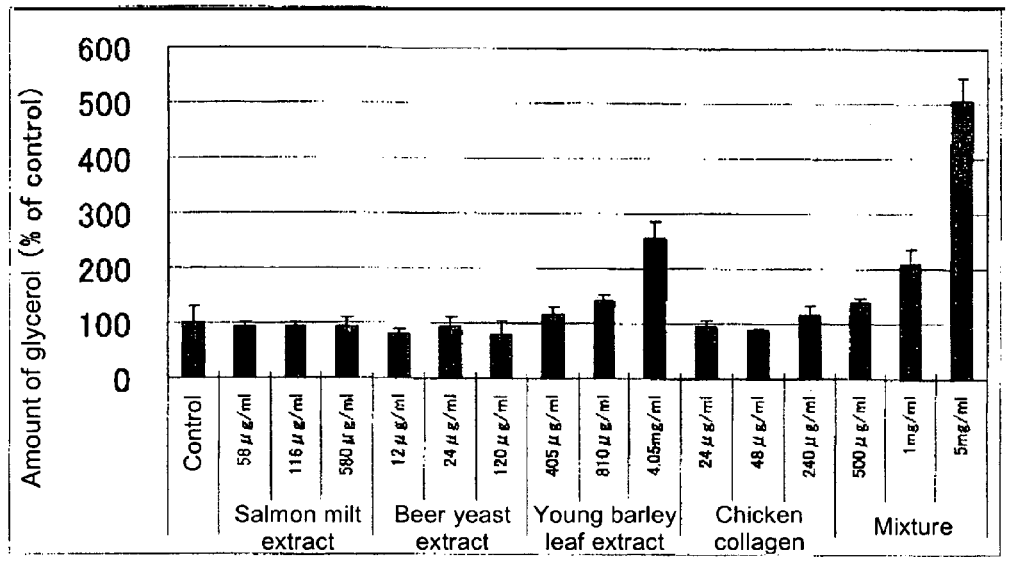
[Figure 2
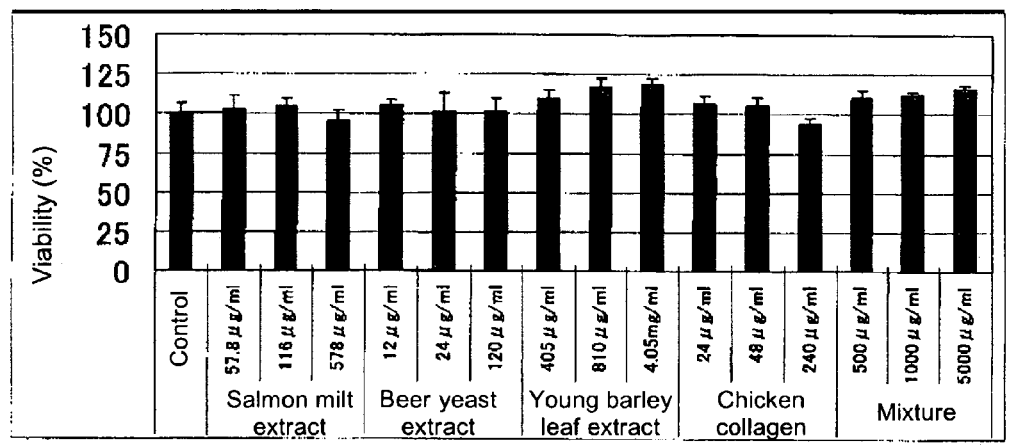

COMPOSITION HAVING LIPOLYSIS-PROMOTING EFFECT

TECHNICAL FIELD

The present invention relates to a composition having a lipolysis-promoting effect wherein a peptic and tryptic digest thereof has an angiotensin-converting enzyme (ACE) inhibitory effect. More specifically, the present invention relates to a composition consisting of a salmon milt extract, a beer yeast extract, a barley grass extract, and chicken collagen, a lipolysis promoter for oral ingestion containing the composition, and an ACE inhibitor for oral ingestion containing the composition.

BACKGROUND ART

Fats result from the accumulation of redundant energies of ingested foods in white adipose tissues. Excessively accumulated white adipose tissues lead to obesity, which consequently causes not only various lifestyle-related diseases but great aesthetic problems. Recently, scientific evidence has demonstrated that, particularly, increase in perivisceral (mesenteric) white adipose tissues triggers hypertension, insulin resistance, abnormal glucose tolerance or hyperlipemia and thereby causes metabolic syndrome. Thus, prevention and improvement thereof have been socially desired.

The hypertrophy of adipose cells attributed to the accumulated fats decreases the secretion of good adipokines from the adipose cells and in turn causes the secretion of various bad adipokines (e.g., TNFα and resistin), resulting in insulin resistance (i.e., reduced insulin sensitivity). As a result, the blood glucose level is insufficiently reduced. Thus, insulin is excessively secreted for controlling the blood glucose level, causing hyperinsulinemia. Upon onset of hyperinsulinemia, the effect of excessive insulin on lipid metabolism, for example, causes metabolic syndrome.

Adiponectin, a good adipokine, promotes the combustion of fatty acids and sugar uptake and improves insulin resistance (non-patent document 1). The combustion effect of adiponectin on fatty acids is not produced by adipose cells, but is attributed to the activation of AMP-activated protein kinase (AMPK) in the liver and skeletal muscles. Adiponectin inhibits gluconeogenesis and stimulates the combustion of fatty acids in the liver, while it stimulates sugar uptake and the combustion of fatty acids in the skeletal muscles.

The expression of adiponectin is induced along with the differentiation of adipose precursor cells into adipose cells. Adiponectin is actively secreted from non-hypertrophied adipose cells. By contrast, adiponectin from hypertrophied adipose cells has an attenuated effect due to the TNFα or the like. In addition, the transcription of adiponectin is inhibited in the hypertrophied adipose cells, and the resulting deficiency of adiponectin causes metabolic abnormality (non-patent document 1).

Vegetable- or fruit-derived carotenoid has been reported to inhibit the differentiation of adipose precursor cells into adipose cells during insulin induction (patent document 1). If the differentiation of adipose precursor cells into adipose cells is inhibited, the expression of adiponectin is also inhibited, as described above. Thus, it is doubtful whether the inhibited differentiation into adipose cells directly leads to an antiobesity effect.

Various studies have previously been conducted on the prevention and improvement of obesity by means of limitations on ingested energies, such as dietary restriction, the delay and inhibition of absorption of excessive energies, or search for carbohydrate absorption inhibitors working in gastrointestinal tracts. The limitations on energy ingestion, however, also serve as factors reducing a basal metabolic rate and do not always improve obesity. Thus, ideally, the accumulated fats are aggressively metabolized and digested and then given off as thermal energies to decrease obesity. From these viewpoints, food materials have been actively searched for functional ingredients having a lipolysis-promoting effect in recent years, and many lipolysis promoters and foods or drinks have been proposed.

Known active ingredients in naturally occurring lipolysis promoters include plants of the family Rutaceae (patent document 2), plants of the genus *Cirsium* (patent document 3), plants of the family Piperaceae (patent document 4), orange leaves, orange flowers, coltsfoot leaves, and calamus roots (patent document 5), and pearl-barley, barley, cassia seeds, guava, and pu-erh tea (patent document 6). Furthermore, examples of lipolysis promoters that have been found recently can include a lipolysis promoter comprising *Nelumbo nucifera* or an extract thereof as an active ingredient (patent document 7), a lipolysis promoter containing at least any of an extract of white birch of the family Betulaceae and an extract of kumazasa of the family Poaceae (patent document 8), and a fat accumulation inhibitor and a promoter containing a hydrolysate of a wheat protein (patent document 9).

Meanwhile, hypertension is a typical symptom of metabolic syndrome and has affected an increasing number of patients year after year. Hypertension is known to cause various complications such as cerebral hemorrhage, subarachnoid hemorrhage, cerebral infarction, myocardial infarction, angina pectoris, and nephrosclerosis. Various studies have been conducted on the pathogenic mechanism of hypertension, and the renin-angiotensin system involved in rise in blood pressure and the kallikrein-kinin system involved in decrease in blood pressure are known to play an important role therein. In the renin-angiotensin system, angiotensinogen secreted from the liver is principally converted to angiotensin I by renin produced in the kidney and further converted to angiotensin II by an angiotensin-converting enzyme (ACE). This angiotensin II contracts vascular smooth muscles and raises blood pressure. On the other hand, kallikrein in the hypotensive system acts on kininogen to produce bradykinin. This bradykinin has the effect of decreasing blood pressure by vasodilation, whereas ACE acts to digest this bradykinin. It has thus been revealed that ACE is involved in a rise in blood pressure by two effects: the production of the hypertensive peptide angiotensin II and the inactivation of the hypotensive peptide bradykinin. Thus, the inhibition of the enzymatic activity of this ACE enables a rise in blood pressure to be prevented. For example, captopril or enalapril, which is a proline derivative developed as a substance having an ACE inhibitory activity, is widely used in the treatment of hypertension.

Also, peptides obtained by enzymatically digesting food material proteins have recently been reported to have an ACE inhibitory activity. There are many reports on, for example, a collagenase digest of gelatin (patent document 10), a tryptic digest of casein (patent documents to 16), a thermolysin digest of γ-casein (patent document 17), a peptic digest of a sardine muscle (patent document 18), a thermolysin digest of dried-bonito shavings (patent document 19), a thermolysin digest of a sesame protein (patent document 20), and peptic and other digests of κ-casein (patent document 21).

PRIOR ART DOCUMENTS

Patent Documents

Patent Document 1: Japanese unexamined Patent Application Publication No. 2003-95930
Patent Document 2: Japanese unexamined Patent Application Publication No. 8-81382
Patent Document 3: Japanese unexamined Patent Application Publication No. 8-301780
Patent Document 4: Japanese unexamined Patent Application Publication No. 8-245410
Patent Document 5: Japanese unexamined Patent Application Publication No. 11-228431
Patent Document 6: Japanese unexamined Patent Application Publication No. 2002-275078
Patent Document 7: Japanese unexamined Patent Application Publication No. 2004-307365
Patent Document 8: Japanese unexamined Patent Application Publication No. 2006-045120
Patent Document 9: Japanese unexamined Patent Application Publication No. 2007-106683
Patent Document 10: Japanese unexamined Patent Application Publication No. 52-148631
Patent Document 11: Japanese unexamined Patent Application Publication No. 58-109425
Patent Document 12: Japanese unexamined Patent Application Publication No. 59-44323
Patent Document 13: Japanese unexamined Patent Application Publication No. 60-23086
Patent Document 14: Japanese unexamined Patent Application Publication No. 60-23087
Patent Document 15: Japanese unexamined Patent Application Publication No. 61-36226
Patent Document 16: Japanese unexamined Patent Application Publication No. 61-36227
Patent Document 17: Japanese unexamined Patent Application Publication No. 2-32127
Patent Document 18: Japanese unexamined Patent Application Publication No. 3-11097
Patent Document 19: Japanese unexamined Patent Application Publication No. 4-144696
Patent Document 20: Japanese unexamined Patent Application Publication No. 8-231588
Patent Document 21: Japanese unexamined Patent Application Publication No. 8-269088

Non-Patent Documents

Non-patent Document 1: Takashi Kadowaki et al., "Adiponectin and Molecular Mechanisms of Diabetes Mellitus/Cardiovascular Disease", Proceedings of the 128th Symposium of the Japanese Association of Medical Sciences "Diabetes Mellitus and Arteriosclerosis", Dec. 2, 2004, p. 34-45

SUMMARY OF THE INVENTION

Object to be Solved by the Invention

An object of the present invention is to provide an orally ingestible composition that has a lipolysis-promoting effect and an ACE inhibitory effect and has no problems with safety as a food such as side effects or toxicity.

Means to Solve the Object

As a result of diligent studies on various food materials for their lipolysis-promoting effects and ACE inhibitory activities, the present inventor has found that: a mixture prepared by using a salmon milt extract, a beer yeast extract, a barley grass extract, and chicken collagen in combination has an excellent lipolysis-promoting effect; and a digested mixture obtained by treating a mixture of a barley grass, a salmon milt extract, a beer yeast extract, and chicken collagen with digestive enzymes pepsin and trypsin exhibits an ACE inhibitory activity. The present invention has been completed on the basis of the findings.

Specifically, the present invention relates to:

(1) a composition comprising a salmon milt extract, a beer yeast extract, a barley grass extract, and chicken collagen, wherein the composition has a lipolysis-promoting effect and a peptic and tryptic digest thereof has an angiotensin-converting enzyme (ACE) inhibitory effect;

(2) the composition according to (1), wherein the composition comprises 14.0 to 14.5 parts by weight of the salmon milt extract, 2.8 to 3.2 parts by weight of the beer yeast extract, and 5.7 to 6.2 parts by weight of the chicken collagen per 100 parts by weight of the barley grass extract;

(3) the composition according to (1) or (2), wherein the salmon milt extract is an extract comprising low-molecular components digested into an oligonucleotide and an oligopeptide obtained by enzymatic treatment of a salmon milt;

(4) the composition according to (1) or (2), wherein the beer yeast extract is an extract comprising a low-molecular RNA component obtained by enzymatic treatment of beer yeast;

(5) the composition according to (1) or (2), wherein the barley grass extract comprises 30% indigestible dextrin;

(6) an oral lipolysis promoter comprising a composition according to any one of (1) to (5);

(7) an oral angiotensin-converting enzyme (ACE) inhibitor comprising a composition according to any one of (1) to (5); and (8) a food or drink comprising a composition according to any one of (1) to (5).

Effect of the Invention

The present invention has enabled a composition having an excellent lipolysis-promoting effect to be provided wherein a digested product thereof has an ACE inhibitory effect. The composition of the present invention has no problems such as side effects or toxicity as a food. Thus, the composition of the present invention can be ingested continuously for a long period and conveniently and is very useful for the prevention or improvement of adult diseases such as obesity and hypertension.

BRIEF DESCRIPTION OF DRAWINGS

FIG. 1 is a diagram showing that the amount of glycerol in the culture supernatant of adipose cells cultured in the presence of a composition of the present invention is significantly increased compared with that in the culture supernatant of adipose cells cultured in the presence of a salmon milt extract, a beer yeast extract, a barley grass extract, or chicken collagen alone. The ordinate of the diagram represents a value in percentage based on the amount of glycerol in the culture supernatant of an unsupplemented group.

FIG. 2 is a diagram showing that no significant difference was observed between the viability of adipose cells cultured in the presence of the composition of the present invention and that of adipose cells cultured in the presence of a salmon milt extract, a beer yeast extract, a barley grass extract, or chicken collagen alone. The ordinate of the diagram represents a value in percentage based on the viability of adipose cells in an unsupplemented group.

MODE OF CARRYING OUT THE INVENTION

Figure 3:
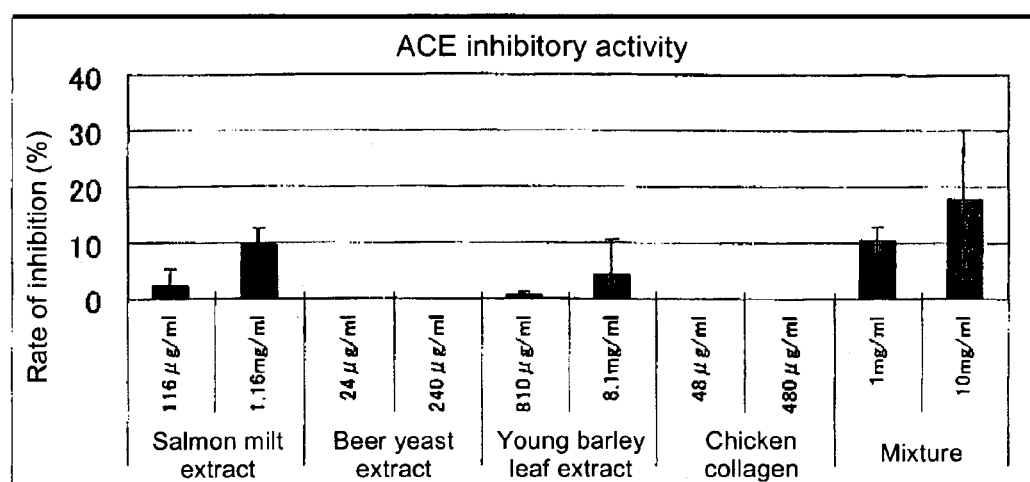
FIG. 3 is a diagram showing that a pepsin- and trypsin-treated product of the composition of the present invention has a significantly excellent ACE inhibitory activity compared with that of a pepsin- and trypsin-treated salmon milt extract, beer yeast extract, barley grass extract, or chicken collagen alone.

A composition of the present invention that has a lipolysis-promoting effect and has an angiotensin-converting enzyme (ACE) inhibitory effect after being digested with pepsin and trypsin is not particularly limited as long as the composition comprises a salmon milt extract, a beer yeast extract, a barley grass extract, and chicken collagen. It is particularly preferable that the composition comprise 14.0 to 14.5 parts by weight of the salmon milt extract, 2.8 to 3.2 parts by weight of the beer yeast extract, and 5.7 to 6.2 parts by weight of the chicken collagen per 100 parts by weight of the barley grass extract.

The salmon milt extract is not particularly limited as long as it can be used for foods. It is preferable that the salmon milt extract comprise low-molecular components digested into an oligonucleotide and an oligopeptide by enzymatic treatment of a salmon milt. A salmon milt extract containing 20 to 50% of an oligonucleotide and an oligopeptide having a molecular weight of 1000 to 3000 is particularly preferable. Such a salmon milt extract is available from, for example, Nissei Bio Co., Ltd.

The beer yeast extract is not particularly limited as long as it can be used for foods. It is preferable that the beer yeast extract comprise a low-molecular RNA by enzymatic treatment of beer yeast. A beer yeast extract containing 20 to 50% RNA having a molecular weight of 1000 to 3000 is particularly preferable. Such a beer yeast extract is available from, for example, Nissei Bio Co., Ltd.

The barley grass extract is not particularly limited, and a barley grass extract spray-dried at a low temperature for foods can be used preferably. The barley grass extract that can be used may comprise indigestible dextrin. Preferable examples of the barley grass extract comprising indigestible dextrin can include a barley grass extract (manufactured by Laxon Corp.) containing 20 to 30% indigestible dextrin.

The chicken collagen is not particularly limited, and chicken collagen for foods can be used preferably. Preferable examples thereof can include chicken collagen manufactured by L S Factory Co., Ltd.

The composition of the present invention can be used as an oral lipolysis promoter as well as an oral fat accumulation inhibitor or obesity-preventing or improving agent. The composition of the present invention can also be used as an oral ACE inhibitor as well as an antihypertensive agent or hypertension-preventing or improving agent with no or exceedingly little side effect after being ingested, unlike synthetic drugs such as captopril. Furthermore, the composition of the present invention can be mixed into a food or drink for use, thereby imparting a lipolysis-promoting effect and an ACE inhibitory effect to the food or drink. As described below in Examples, the composition of the present invention exhibits an excellent ACE inhibitory effect after being digested with digestive enzymes pepsin and trypsin. Thus, the composition of the present invention orally ingested as a food can exert a hypertension-preventing or improving effect. For mixing the composition of the present invention into a food or drink for use, an effective amount of the active ingredient is added and mixed into, for example, a raw material for the production of the food or drink or a produced food or drink product. In this context, the "effective amount of the active ingredient" means a content of the active ingredient ingested as an individual food or drink taken in a usual amount and can be determined depending on the age and body weight of a recipient, symptoms, administration times, dosage forms, administration methods, the combination of drugs, etc.

The food or drink of the present invention is not particularly limited as long as it contains the composition of the present invention. Specific examples thereof can include a food or drink or a supplement directly prepared from the composition of the present invention, the composition of the present invention further mixed with various proteins, sugars, fats, trace elements, vitamins, etc., such a composition prepared into a liquid, semi-liquid or solid state, and a general food or drink supplemented or mixed with the composition of the present invention.

Furthermore, the food or drink of the present invention may be a health food, a functional food, a food for specified health use, or a food for invalids. The oral lipolysis promoter, the oral ACE inhibitor, and the food or drink of the present invention can be produced using additives or compounding ingredients usually used, for example, auxiliaries such as excipients, expanders, binders, disintegrants, lubricants, dispersants, preservatives, wetting agents, solubilizers, antiseptics, stabilizers, capsule bases, and food materials. Specific examples of components in the auxiliaries can include lactose, fructose, glucose, starch, gelatin, magnesium carbonate, synthetic magnesium silicate, talc, magnesium stearate, calcium carbonate, methylcellulose, carboxymethylcellulose or salts thereof, gum arabic, polyethylene glycol, syrup, Vaseline, glycerin, ethanol, propylene glycol, citric acid, sodium chloride, sodium sulfite, sodium phosphate, pullulan, carrageenan, dextrin, reduced palatinose, sorbitol, xylitol, stevia, synthetic sweeteners, citric acid, ascorbic acid, acidulants, sodium bicarbonate, sucrose ester, hydrogenated plant fats and oils, potassium chloride, safflower oil, beeswax, soybean lecithin, and flavors.

Hereinafter, the present invention will be described specifically with reference to Examples. However, the technical scope of the present invention is not limited to these examples.

Example 1

(1) Preparation of Samples

In Examples of the present invention, samples used in evaluations were prepared by using a salmon milt extract (manufactured by Nissei Bio Co., Ltd.), a beer yeast extract (manufactured by Nissei Bio Co., Ltd.), a barley grass extract (manufactured by Laxon Corp.; containing 30% indigestible dextrin), and chicken collagen (manufactured by L S Factory Co., Ltd.) singly or in combination. The concentration of each component used in the preparation of samples is shown in Table 1.

TABLE 1

| Material | Sample 1 | Sample 2 | Sample 3 | Sample 4 |
|---|---|---|---|---|
| ① Barley grass extract | 405 µg/ml | 810 µg/ml | 4.05 mg/ml | 8.1 mg/ml |
| ② Salmon milt extract | 58 µg/ml | 116 µg/ml | 580 µg/ml | 1.16 mg/ml |
| ③ Beer yeast extract | 12 µg/ml | 24 µg/ml | 120 µg/ml | 240 µg/ml |

TABLE 1-continued

| Material | Sample 1 | Sample 2 | Sample 3 | Sample 4 |
|---|---|---|---|---|
| ④ Chicken collagen | 24 µg/ml | 48 µg/ml | 240 µg/ml | 480 µg/ml |
| ⑤ Mixture (①+②+③+④) | 500 µg/ml | 1 mg/ml | 5 mg/ml | 10 mg/ml |

(2) Differentiation into Adipose Cells and Assay of Lipolytic Activity

Mouse adipose precursor cell line 3T3-L1 cells were inoculated at a concentration of $3 \times 10^4$ cells/250 µl/well to a 96-well culture plate, preincubated for 2 days using a DMEM medium containing 10% CS (10% CS/DMEM), and cultured until confluence (day 0). An adipose cell differentiation inducer [0.5 mM isobutylmethylxanthine (IBMX), 1 µM dexamethasone (DEX), and 10 µg/ml insulin] was further added to the medium, and the cells were further cultured for 3 days to induce their differentiation into adipose cells. The cells thus induced for differentiation were cultured for 3 days in a 10% FBS/DMEM medium containing 10 µg/ml insulin and then cultured for 6 days in a basic medium. During this 6-day culture, the medium was replaced every two days to accumulate fat droplets. Then, the mixture described in Table 1 or the salmon milt extract, the beer yeast extract, the barley grass extract, or the chicken collagen alone was added thereto, and the cells were further cultured for hours. After the completion of culture, each supernatant was collected, and the amount of glycerol in the culture supernatant was determined using Adipolysis assay kit. This amount of glycerol in the culture supernatant was used as an index for lipolysis. The rate of glycerol release is a relative value to the value of a control as 100%.

Rate of lipolysis promotion %=[A/B]×100

A: amount of free glycerol in a sample supplemented with the extract(s)
B: amount of free glycerol in a sample unsupplemented with any extract.

(3) Test Results

As described above, the lipolysis-promoting effect was determined with the measured value of the amount of glycerol formed by lipolysis as an index. A graph of the results is shown in FIG. 1, and numeric values thereof are shown in Table 2. The groups supplemented with the mixture (sample) containing the barley grass extract exhibited values of 208.67% and 504.17% relative to the control at their concentrations of 1 mg/ml and 5 mg/ml, respectively. By contrast, the groups supplemented with each component alone exhibited lipolysis rates of 141.57% in the 810 µg/ml barley extract-supplemented group, 255.22% in the 4.05 mg/ml barley extract-supplemented group, 95% in the 116 µg/ml salmon milt extract-supplemented group, 95.44% in the 580 µg/ml salmon milt extract-supplemented group, 95% in the 24 µg/ml beer yeast extract-supplemented group, 81.6% in the 120 µg/ml beer yeast extract-supplemented group, 87.67% in the 48 µg/ml chicken collagen-supplemented group, and 116.7% in the 240 µg/ml chicken collagen-supplemented group. These results demonstrated that the significant lipolysis-promoting effect exhibited by the samples prepared by using the components barley grass extract, salmon milt extract, beer yeast extract, and chicken collagen in combination was not confirmed in the samples prepared by using each component alone, and showed that significant synergistic effect was confirmed by using the components barley grass extract, salmon milt extract, beer yeast extract, chicken collagen in combination.

TABLE 2

| | | |
|---|---|---|
| Control | | 100.0 |
| Barley grass extract | 405 µg/ml | 117.1 |
| | 810 µg/ml | 141.6 |
| | 4.05 mg/ml | 255.2 |
| Salmon milt extract | 58 µg/ml | 95.8 |
| | 116 µg/ml | 95.0 |
| | 580 µg/ml | 95.4 |
| Beer yeast extract | 12 µg/ml | 81.5 |
| | 24 µg/ml | 95.0 |
| | 120 µg/ml | 81.6 |
| Chicken collagen | 24 µg/ml | 95.6 |
| | 48 µg/ml | 87.7 |
| | 240 µg/ml | 116.7 |
| Mixture | 500 µg/ml | 138.7 |
| | 1 mg/ml | 208.7 |
| | 5 mg/ml | 504.2 |

(4) Assay of Viability of Cells

After the collection of the supernatant, the viability of the cells in each sample was further assayed using Cell counting Kit-8 (manufactured by Dojindo). The results shown in FIG. 2 demonstrated that no difference in the viability was confirmed among the groups supplemented with the mixture or each component.

Example 2

(1) Preparation of Peptic and Tryptic Digests of Sample and Each Component

A 10% solution of the mixture shown in Table 1 or each component was prepared using 0.1 M HCl.KCl (pH 2.5). Pepsin was added to each solution to perform enzymatic treatment at 37° C. for 2.5 hours. The solution thus treated was heated at 90° C. for 10 minutes in a boiling water bath to inactivate pepsin. This treated solution was diluted 5-fold using a 0.1 M potassium phosphate buffer (pH 7.5). Trypsin was added thereto to further perform enzymatic treatment at 37° C. for 24 hours. The solution thus treated was heated at 90° C. for 10 minutes in a boiling water bath to inactivate trypsin. This treated solution was centrifuged, and the supernatant was freeze-dried and used in the subsequent experiment.

(2) Assay of Angiotensin-Converting Enzyme (ACE) Inhibitory Activity

The ACE inhibitory activity was assayed on the basis of a modification of Lieberman assay. Each freeze-dried sample thus enzymatically treated was prepared into a concentration shown in Table 1, which was the same as that before the enzymatic treatment. To this prepared solution (30 µL), a Hip-His-Leu substrate solution (250 µl) diluted to 5 mM with a borate buffer (pH 8.3) containing 400 mM NaCl was added, and the mixture was incubated in a constant-temperature water bath of 37° C. for 5 minutes. A 600 mu/ml (6 mU) ACE solution (100 µl) was added thereto, and the mixture was immediately stirred and then reacted at 37° C. for 60 minutes. The reaction was stopped by addition of 1 N hydrochloric acid (250 µl) and stirring. Then, ethyl acetate (1.5 ml) was added to the reaction solution, and the mixture was sufficiently stirred to release hippuric acid. After centrifugation at 3,000 rpm for 10 minutes, 1.0 ml of the ethyl acetate layer was collected as the upper layer and evaporated to dryness using an evaporator. The residue was further dried for 60 minutes in a reduced-pressure desiccator. Then, 3 ml of ultrapure water was added thereto, and the absorbance of the resulting solution was measured at 228 nm. The inhibitory activity was calculated as a rate of inhibition (%) according to the following equation:

Rate of inhibition (%)=$\{(E_C-E_S)/(E_C-E_B)\} \times 100$

In the equation, $E_S$ represents the absorbance of a solution supplemented with the sample solution; $E_C$ represents the absorbance of a solution supplemented with ultrapure water instead of the sample solution; and $E_B$ represents the absorbance of a solution reacted by addition of 1 N hydrochloric acid in advance.

(3) Test Results

The results shown in FIG. 3 demonstrated that the group supplemented with the 1 mg/ml or 10 mg/ml mixture exhibited a significantly high ACE inhibitory activity compared with the group supplemented with each composition alone at the corresponding concentration. Thus, synergistic effect was confirmed.

Example 3

1687 mg of a barley grass extract, 240 mg of a salmon milt extract, 50 mg of a beer yeast extract, 100 mg of chicken collagen, 723 mg of indigestible dextrin, and 500 mg of dextrin per stick were mixed to prepare stick-type supplements.

The invention claimed is:

1. An oral lipolysis promoter composition comprising a salmon milt extract, a beer yeast extract, a barley grass extract, and chicken collagen, wherein the composition comprises 14.0 to 14.5 parts by weight of the salmon milt extract, 2.8 to 3.2 parts by weight of the beer yeast extract, and 5.7 to 6.2 parts by weight of the chicken collagen per 100 parts by weight of the barley grass extract, and wherein the composition has a lipolysis-promoting effect and a peptic and tryptic digest thereof has an angiotensin-converting enzyme (ACE) inhibitory effect.

2. The oral lipolysis promoter composition according to claim 1, wherein the salmon milt extract is an extract comprising components having a molecular weight of 1000 to 3000 digested into an oligonucleotide and an oligopeptide, obtained by enzymatic treatment of a salmon milt.

3. The oral lipolysis promoter composition according to claim 1, wherein the beer yeast extract is an extract comprising a RNA component having a molecular weight of 1000 to 3000 obtained by enzymatic treatment of beer yeast.

4. The oral lipolysis promoter composition according to claim 1, wherein the barley grass extract comprises 30% indigestible dextrin.

\* \* \* \* \*